(12) United States Patent
Lin

(10) Patent No.: US 11,654,169 B2
(45) Date of Patent: May 23, 2023

(54) METHODS FOR PROTECTING SKIN AND/OR PROMOTING WOUND HEALING

(71) Applicant: SINPHAR PHARMACEUTICAL CO., LTD., Dongshan Township, Yilan County (TW)

(72) Inventor: Hang-Ching Lin, Dongshan Township, Yilan County (TW)

(73) Assignee: SINPHAR PHARMACEUTICAL CO., LTD., Dongshan Township, Yilan County (TW)

( * ) Notice: Subject to any disclaimer, the term of this patent is extended or adjusted under 35 U.S.C. 154(b) by 0 days.

(21) Appl. No.: 15/695,527

(22) Filed: Sep. 5, 2017

(65) Prior Publication Data

US 2018/0064771 A1 Mar. 8, 2018
US 2018/0064771 A1 Mar. 8, 2018

Related U.S. Application Data

(60) Provisional application No. 62/383,860, filed on Sep. 6, 2016.

(51) Int. Cl.

| | |
|---|---|
| *A61K 36/076* | (2006.01) |
| *A61K 9/06* | (2006.01) |
| *A61K 31/194* | (2006.01) |
| *A61K 31/575* | (2006.01) |
| *A61K 8/9728* | (2017.01) |
| *A61K 8/63* | (2006.01) |
| *A61Q 19/08* | (2006.01) |
| *A61K 9/00* | (2006.01) |
| *A61K 31/19* | (2006.01) |
| *A61K 31/728* | (2006.01) |
| *A61Q 19/00* | (2006.01) |
| *A61K 31/375* | (2006.01) |
| *A61K 45/06* | (2006.01) |

(52) U.S. Cl.
CPC .............. *A61K 36/076* (2013.01); *A61K 8/63* (2013.01); *A61K 8/9728* (2017.08); *A61K 9/0014* (2013.01); *A61K 9/06* (2013.01); *A61K 31/19* (2013.01); *A61K 31/194* (2013.01); *A61K 31/575* (2013.01); *A61K 31/728* (2013.01); *A61Q 19/00* (2013.01); *A61Q 19/08* (2013.01); *A61K 31/375* (2013.01); *A61K 45/06* (2013.01); *A61K 2236/00* (2013.01); *A61K 2800/522* (2013.01)

(58) Field of Classification Search
CPC .......... A61K 2236/00; A61K 2800/522; A61K 31/19; A61K 31/375; A61K 31/575; A61K 31/728; A61K 36/076; A61K 45/06; A61K 8/63; A61K 8/9728; A61K 9/0014; A61K 9/06; A61K 31/194; A61P 17/02; A61P 17/16; A61P 43/00; A61Q 19/00; A61Q 19/08

USPC .......................................................... 514/94
See application file for complete search history.

(56) References Cited

U.S. PATENT DOCUMENTS

| | | | | |
|---|---|---|---|---|
| 5,716,800 | A * | 2/1998 | Meybeck ................. | A61K 8/99 435/254.1 |
| 7,992,280 | B2 * | 8/2011 | Fader ................... | B60G 21/055 164/464 |
| 8,658,629 | B2 * | 2/2014 | Lin ...................... | A61K 9/1652 514/180 |
| 9,333,231 | B2 * | 5/2016 | Cheng .................... | A61K 36/06 |
| 9,370,540 | B2 * | 6/2016 | Lin ......................... | C07J 9/005 |
| 9,757,392 | B2 * | 9/2017 | Lin ...................... | A61K 9/4866 |
| 10,588,927 | B2 * | 3/2020 | Choi .................... | A61K 36/605 |
| 10,864,238 | B2 * | 12/2020 | Choi .................... | A61K 36/076 |
| 2003/0124159 | A1 | 7/2003 | Jenkins et al. | |
| 2009/0247496 | A1 * | 10/2009 | Lin ........................ | A61K 9/485 514/181 |
| 2009/0318399 | A1 * | 12/2009 | Lin ........................ | A61K 31/56 514/180 |
| 2012/0189651 | A1 * | 7/2012 | John ....................... | A61P 37/08 424/195.15 |
| 2015/0335690 | A1 | 11/2015 | Lin et al. | |

FOREIGN PATENT DOCUMENTS

| | | |
|---|---|---|
| CA | 2839511 | 12/2012 |
| CN | 103974715 | 8/2014 |
| CN | 104688782 | 6/2015 |
| CN | 105147592 | 12/2015 |
| CN | 105639617 | 6/2016 |
| DE | 10151649 | 5/2003 |
| JP | 09-40552 | 2/1997 |
| JP | 10-237093 | 9/1998 |
| KR | 10-2015-0057898 | 5/2015 |
| KR | 10-2016-0057196 | 5/2016 |
| TW | 201408332 | 3/2014 |

OTHER PUBLICATIONS

Tai et al. (Triterpenes from the Surface Layer of Poria cocos, Photochemistry. 1995. vol. 39, No. 5. pp. 1165-1169).*

(Continued)

*Primary Examiner* — Rei Tsang Shiao

(74) *Attorney, Agent, or Firm* — Ping Wang; Rimon Law

(57) ABSTRACT

A method for at least one of protecting skin and promoting wound healing is provided. The method comprises administering to a subject in need an effective amount of *Poria cocos* extract, dehydropachymic acid (DPA), pachymic acid (PA), dehydrotumulosic acid (DTA), tumulosic acid (TA), polyporenic acid C (PAC), 3-epi-dehydrotumulosic acid (EDTA), dehydrotrametenolic acid (DTTA), trametenolic acid (TTA), dehydroeburicoic acid (DEA), eburicoic acid (EA), poricoic acid A (PAA) and/or poricoic acid B (PAB).

4 Claims, No Drawings

(56) References Cited

OTHER PUBLICATIONS

Cuellar et al. "Effect of the Basidiomycete Poria cocos on Experimental Dermatitis and Other Inflammatory Conditions". (Chemical and Pharmaceutical Bulletin, 1997. vol. 45, No. 3. pp. 492-494).*
Fu-Lun Li et al. (Evid Based Complement Alternat Med.2012; 2012: 930192.Published online May 14, 2012. doi: 10.1155/2012/930192).*
Yang PF, Liu C, Wang HQ, Li JC, Wang ZZ, Xiao W, Chen RY. [Chemical constituents of Poria cocos]. Zhongguo Zhong Yao Za Zhi. Mar. 2014;39(6):1030-3. Chinese. PMID: 24956845, Abstract.*
Wittmann et al. J Trauma, 2005, 59(1): 162-8 (abstract).*
Price et al. Am J Clin Dermatol, 2005, 6(6): 393-402 (abstract).*
Cheng, S.M., et al., "Antioxidant Properties of Triterpenes from Poria cocos Peel", Food Science, 2011, vol. 32, No. 09, pp. 27-30.
Cheng, S.M., et al., "Analysis of the Whitening Active of Triterpenoids from Poria cocos Peel and Mechanism of Tyrosinase Inhibition", Food Research And Development; 2016, vol. 37, No. 09, pp. 18-22.
Ma-Ling et al., Research progress of Poria cocos, Asia-Pacific Traditional Medicine, Jun. 2015, vol. 11, No. 12: 55-59.
Poria cocos mushroom, unveil its skin improvement effectl BeautyNuri Cosmetic Paper (Jul. 2, 2010).
Kawagishi et al. "Novel hydroquinone as a matrix metalloproteinase inhibitor from the muchroom, Piptoporus betulinus". Biosci Biotechnol Biochem. Dec. 2002,66(12):2748-2750.

\* cited by examiner

METHODS FOR PROTECTING SKIN AND/OR PROMOTING WOUND HEALING

FIELD OF THE INVENTION

The present invention relates to a method for at least one of protecting skin and promoting wound healing, and particularly relates to the uses of the *Poria cocos* extract and/or its active ingredient(s) in at least one of protecting skin and promoting wound healing. Since *Poria cocos* extract and its active ingredient(s) are effective in enhancing the expression of collagen and/or hyaluronic acid, they can protect skin and/or promote wound healing.

BACKGROUND OF THE INVENTION

When the moisture content of skin decreases, keratinocytes would accumulate on the surface of skin because they cannot shed normally, and this would cause the skin to lose luster and elasticity and to look dry and rough. Aging skin, such as wrinkles, even starts happening. Therefore, if the moisture content of skin can be enhanced effectively, it will reduce the occurrence of the above situations.

Research has confirmed that collagen and hyaluronic acid can enhance the moisture content of skin. Accordingly, many care products and healthy foods with externally added collagen and/or hyaluronic acid that are currently on the market advertise the effects of nourishing skin, tightening skin, repairing skin, retaining moisture, smoothing wrinkles, delaying skin-aging, and preventing skin-aging. In addition, because collagen has high biocompatibility and hypo-immunity, and can be absorbed and decomposed by the human body, there are also healthy foods with externally added collagen that advertise a wound-healing effect.

However, in recent years, the outbreak of zoonoses (such as foot-and-mouth disease, avian influenza and mad cow disease) around the world has jeopardized the safety of animal collagen and hyaluronic acid. In addition, the exogenous collagen or hyaluronic acid has poor absorption rate and induction of immune response no matter the method of administration, such as oral administration, percutaneous administration or injection. Because of the above problems, the use of exogenous collagen and hyaluronic acid has been controversial in the industry. Therefore, people are actively developing the preparations or methods that are effective in enhancing the expression of endogenous collagen and/or hyaluronic acid. By enhancing the expression of endogenous collagen and/or hyaluronic acid, the effects of protecting skin and/or promoting wound healing can be achieved, and the safety and availability issues caused by supplementing exogenous collagen and/or hyaluronic acid can be avoided.

Inventors of the present invention found that the *Poria cocos* extract and/or its active ingredients can effectively enhance the contents of intracellular collagen, extracellular collagen and/or extracellular hyaluronic acid. That is, *Poria cocos* extract and/or its active ingredients can effectively enhance the content of endogenous collagen and/or hyaluronic acid, and thus *Poria cocos* extract and/or its active ingredients can be used for at least one of protecting skin and promoting wound healing.

SUMMARY OF THE INVENTION

Therefore, one objective of the present invention is to provide a use of *Poria cocos* extract in the manufacture of a preparation, wherein the preparation is for at least one of protecting skin and promoting wound healing. Preferably, the *Poria cocos* extract comprises at least one of dehydropachymic acid (DPA), pachymic acid (PA), dehydrotumulosic acid (DTA), tumulosic acid (TA), polyporenic acid C (PAC), 3-epi-dehydrotumulosic acid (EDTA), dehydrotrametenolic acid (DTTA), trametenolic acid (TTA), dehydroeburicoic acid (DEA), eburicoic acid (EA), poricoic acid A (PAA) and poricoic acid B (PAB). More preferably, the *Poria cocos* extract is a *Poria cocos* epidermis extract, wherein in the *Poria cocos* epidermis extract, the total amount of poricoic acid A and poricoic acid B is at least 40 wt %, based on the total weight of the *Poria cocos* epidermis extract.

Another objective of the present invention is to provide a use of an active ingredient in the manufacture of a preparation, wherein the preparation is for at least one of protecting skin and promoting wound healing, and the active ingredient is selected from at least one of dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A and poricoic acid B. Preferably, the active ingredient is poricoic acid A and/or poricoic acid B. More preferably, the active ingredient is provided as an extract, especially as a fungal extract or plant extract.

Preferably, the above preparation is provided as a cosmetic, a care product, a food or a medicament. Since the medicament is effective in enhancing the expression of collagen and/or hyaluronic acid, it can promote wound healing. Since the cosmetic, care product and food are effective in enhancing the expression of collagen and/or hyaluronic acid, they can protect skin, and thus, can be used for at least one of nourishing skin, tightening skin, repairing skin, retaining moisture, smoothing wrinkles, delaying skin-aging, and preventing skin-aging.

Still another objective of the present invention is to provide a method for at least one of protecting skin and promoting wound healing, comprising administering to a subject in need an effective amount of the above active ingredient or *Poria cocos* extract.

Still another objective of the present invention is to provide a composition for at least one of protecting skin and promoting wound healing, wherein the composition is a cosmetic, a care product, a food or a medicament, and comprises an effective amount of the above active ingredient or *Poria cocos* extract.

The detailed technology and some of the embodiments implemented for the present invention are described in the following paragraphs for people skilled in this field to well appreciate the features of the claimed invention.

DESCRIPTION OF THE PREFERRED EMBODIMENTS

The following will describe some of the embodiments of the present invention. However, without departing from the spirit of the present invention, the present invention may be embodied in various embodiments and should not be limited to the embodiment described in the specification. In addition, unless otherwise indicated herein, the expression "a," "an," "the," or the like recited in the specification of the present invention (especially in the claims) are intended to include both the singular and plural forms. The term "an effective amount" used in this specification refers to the amount of the compound that can effectively enhance the expression of collagen and/or hyaluronic acid in a subject when administered to the subject. The term "subject" used in this specification refers to a mammalian, including human and non-human animals. The unit "mg/kg-body weight" used in this specification refers to the dosage required per kg of body weight.

As described above, the reduction of moisture content in skin is an important factor of skin-aging. It is known that collagen is an important glycoprotein both in human connective tissue and extracellular matrix, and it accounts for more than 20% of the total protein in human body. The basic structure of collagen is a triple helix, which is formed with three polypeptide chains winding around each other. The triple helical structures are synthesized in skin fibroblasts, and then they will be secreted into extracellular matrix to form tight, mature collagen fibers. The structures allow the collagens to keep the skin elastic, increase the moisture content of skin and promote wound healing. As for hyaluronic acid, it is abundantly present in the dermis. Hyaluronic acids are mucopolysaccharides and are an effective moisturizer, and thus, can be used to keep the skin's elasticity and moisture content, and can reduce wrinkles and prevent skin aging.

Herbal FU-LING refers to the dried sclerotium of *Poria cocos* (Schw.) Wolf, a fungus in the family Fomitopsidaceae. *Poria cocos* (FU-LING) fungus often parasitizes the roots of pine trees. The external layer of *Poria cocos* (FU-LING) is of a light or dark brown color (*Poria cocos* epidermis) and the inside of *Poria cocos* (FU-LING) is of a pink or white color (*Poria cocos* meat). According to traditional Chinese medicine classics, *Poria cocos* is used in sedation, diuresis, nutrient supplementation, immunity enhancement, aging delay, etc. Modern medical research also confirms that *Poria cocos* has anti-inflammation, anti-tumor, immune system regulation, blood glucose reduction, nutrient-absorbed promotion and other functions. Inventors of the present invention found that *Poria cocos* extract can promote the expression of collagen and/or hyaluronic acid (i.e., enhancing the content of endogenous collagen and/or hyaluronic acid) in cells, effectively. Accordingly, *Poria cocos* extract can be used for protecting skin and promoting wound healing.

Therefore, the present invention provides the uses of *Poria cocos* extract in protecting skin and/or promoting wound healing, including a use of *Poria cocos* extract in the manufacture of a preparation for protecting skin and/or promoting wound healing; a method for protecting skin and/or promoting wound healing comprising administering the *Poria cocos* extract to a subject in need; and a composition comprising the *Poria cocos* extract.

According to the present invention, the *Poria cocos* extract can be a crude extract or an extract provided by an operation comprising the following steps: (a) extracting *Poria cocos* (i.e., raw material) with a first polar solvent to provide a crude extract; (b) drying the crude extract to provide a crude extract powder; (c) extracting the crude extract powder with a second polar solvent to provide a *Poria cocos* extract. The first polar solvent and the second polar solvent are the same or different and are respectively selected from a group consisting of water, ethanol and combinations thereof. In some embodiments of the present invention, aqueous ethanol solutions with the same or different ethanol concentrations were used as the first polar solvent and the second polar solvent.

In step (a), the raw material can be *Poria cocos* epidermis and/or *Poria cocos* meat. The ratio of the amounts of the first polar solvent and the raw material can be optionally adjusted. In general, there is no particular limitation to the amount of first polar solvent being used, as long as the materials can be dispersed in the first polar solvent evenly. For example, in step (a), the first polar solvent and the raw material can be used at a volume ratio ranging from about 8:1 to about 16:1 (first polar solvent:the raw material). In one embodiment of the present invention, the extraction of step (a) was carried out with the use of *Poria cocos* epidermis (as the raw material) and an aqueous ethanol solution (as the first polar solvent) at a volume ratio of aqueous ethanol solution to the raw material of 8:1. In another embodiment of the present invention, the extraction of step (a) was carried out with the use of *Poria cocos* epidermis and meat (as the raw material) and an aqueous ethanol solution (as the first polar solvent) at a volume ratio of aqueous ethanol solution to the raw material of 8:1.

In step (a), the extraction can be conducted for a suitable period of time depending on the adoption of the first polar solvent. When an aqueous ethanol solution is used as the first polar solvent and the volume ratio of aqueous ethanol solution: *Poria cocos* is 8:1, the extraction is usually conducted for at least 1 hour, preferably at least 2 hours, and more preferably at least 3 hours. Step (a) can be optionally accompanied with other operations such as decoction, cooling, filtration, vacuum concentration, and resin column chromatography. Optionally, the *Poria cocos* can be pre-soaked in the first polar solvent for a period of time prior to conducting step (a). For example, *Poria cocos* can be pre-soaked in the first polar solvent for about 12 hours when an aqueous ethanol solution is served as the first polar solvent.

In step (c), the ratio of the amounts of second polar solvent and the crude extract powder obtained from step (b) can be optionally adjusted. In general, there is no particular limitation to the amount of second polar solvent that is used, as long as the crude extract powder can be dispersed in the second polar solvent evenly. For example, in step (c), the second polar solvent and the crude extract powder of *Poria cocos* can be used at a volume ratio ranging from about 8:1 to about 16:1 (first polar solvent:crude extract powder of *Poria cocos*). In one embodiment of the present invention, the extraction of step (c) was carried out with the use of an aqueous ethanol solution as the second polar solvent and at a volume ratio of aqueous ethanol solution to the crude extract powder of *Poria cocos* of 8:1.

The *Poria cocos* extract adopted in accordance with the present invention can be a dry matter, which can be provided by drying the liquid extract obtained from step (c). To achieve as high of an extraction efficiency as possible, the extraction of *Poria cocos* can be optionally repeated with the same or different first polar solvents prior to step (b), and the liquid extracts thus obtained can be combined to provide the crude extract for use in step (b). Also, step (b), step (c), and the cycle of other optional operations described above can be repeated.

As shown in the following examples, according to the present invention, ingredients such as dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A, poricoic acid B can be purified and isolated from the *Poria cocos* extract.

Inventors of the present invention further found that dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A and poricoic acid B can all effectively promote cells to express collagen and/or hyaluronic acid (i.e., enhancing the content of endogenous collagen and/or hyaluronic acid), and thus, they can be used in protecting skin and promoting wound healing. Therefore, the present invention also relates to the uses of an active ingredient in protecting skin and/or promoting wound healing, wherein the active ingredient is selected from at least one of dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A and poricoic acid B. The above uses comprise a use of the active ingredient in the manufacture of a preparation for protecting skin and promoting wound healing; a method for protecting skin and/or promoting wound healing comprising administering the active ingredient to a subject in need; and a composition comprising the active ingredient. Preferably, the active ingredient adopted in accordance with the present invention is provides as an extract. More preferably, the active ingredient is provided as a fungal extract or plant extract.

According to the present invention, the preparation or composition is provided as a cosmetic, a care product, a food or a medicament. When the preparation or composition is provided as a cosmetic or a care product, depending on the desired purpose, the cosmetic or care product can be provided in any suitable form without particular limitation. For example, the cosmetic or care product can be provided in the form of an emulsion, a cream, a gel (e.g., a hydrogel), a paste (e.g., a dispersing paste, an ointment), a spray, or a solution (e.g., a washing liquid, a suspension) for external use, but is not limited thereby. Alternatively, the preparation or composition of the present invention can be manufactured into a food for swallowing or drinking, such as a healthy food, a beauty beverage etc. In addition, the preparation or composition of the present invention could be also provided in a form of an injection for subcutaneous administration.

Similarly, when the preparation or composition is provided as a medicament, depending on the desired purpose, the medicament can be provided in any suitable form without particular limitation. For example, the medicaments can be administered to a subject in need by an oral or parenteral (e.g., percutaneous, subcutaneous or intravenous) route to protect skin and/or promote wound healing, but the administration is not limited thereby. Depending on the form and purpose, suitable carriers could be chosen and used to provide the medicaments, wherein the carriers include excipients, diluents, auxiliaries, stabilizers, absorbent retarders, disintegrating agents, hydrotropic agents, emulsifiers, antioxidants, adhesives, binders, tackifiers, dispersants, suspending agents, lubricants, and/or hygroscopic agents, etc.

As a dosage form for oral administration, the medicament can comprise any pharmaceutically acceptable carrier that will not adversely affect the desired effects of the active ingredients (i.e., at least one of *Poria cocos* extract, dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A and poricoic acid B). For example, the pharmaceutically acceptable carrier can be water, saline, dextrose, glycerol, ethanol or its analogs, cellulose, starch, sugar bentonite, and combinations thereof. The medicament can be provided in any suitable form for oral administration, such as in the form of a tablet (e.g., dragees), a pill, a capsule, granules, a pulvis, a fluidextract, a solution, a syrup, a suspension, a tincture, etc.

As for the form of injections or drips suitable for subcutaneous or intravenous, the medicament can comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the medicament as an intravenous, an emulsified intravenous infusion, a powder for injection, a suspension for injection, or a powder suspension for injection, etc. Alternatively, the medicament can be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need.

Optionally, the preparation or composition provided according to the present invention could further comprise a suitable amount of additives, such as a flavoring agent, a toner, or a coloring agent for enhancing the palatability and the visual perception of the preparation or composition, and/or a buffer, a conservative, a preservative, an antibacterial agent, or an antifungal agent for improving the stability and storability of the preparation or composition. In addition, the preparation or composition can optionally further comprise one or more other active ingredient(s) (e.g., collagen, hyaluronic acid, elastin, mandelic acid, arbutin, etc.), or be used in combination with a cosmetic or medicament comprising one or more other active ingredient(s), to further enhance the effects of the preparation or composition, or to increase the application flexibility and adaptability of the preparation or composition thus provided, as long as the other active ingredients do not adversely affect the desired effects of the preparation or composition of the present invention.

Depending on the need, age, body weight, and health conditions of the subject, the preparation or composition provided according to the present invention can be dosed at various administration frequencies, such as once a day, multiple times a day, or once every few days, etc.

The present invention also provides a method for at least one of protecting skin and promoting wound healing, comprising administering to a subject in need an effective amount of an active ingredient (i.e., at least one of *Poria cocos* extract, dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A and poricoic acid B). In the method for at least one of protecting skin and promoting wound healing according to the present invention, the type, applied route, applied form, suitable dosage and use of the active ingredients in related treatment are all in line with the above description.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

PREPARATION EXAMPLES

A. Preparation of *Poria cocos* Extract

A-1. *Poria cocos* (also called as herbal FU-LING; habitat: Yunnan, China) was washed and its skin was peeled (hereinafter referred to as "*Poria cocos* epidermis"), and the rest was meat (hereinafter referred to as "*Poria cocos* meat").

A-2. The *Poria cocos* epidermis obtained from A-1 was soaked in 75% aqueous ethanol solution (*Poria cocos* epidermis:75% aqueous ethanol solution=1:8 in volume) at room temperature for 12 hours, and then decocted for 3 hours to provide a liquid extract. The foregoing extraction procedures were repeated three times. The liquid extracts obtained from the three extractions were combined and filtered to remove the insoluble and provide a crude extract. The solvent contained in the crude extract was removed by vacuum concentration to provide a concentrated solution. The concentrated solution was dried by using a spray dryer to provide a crude extract powder.

A-3. The crude extract powder obtained from A-2 was extracted with 95% aqueous ethanol solution (crude extract powder:95% aqueous ethanol solution=1:8 in volume) for 3 hours, and then the liquid extract obtained therefrom was eluted by a column with a stationary phase of silica gel to provide a *Poria cocos* epidermis extract.

A-4. The component of *Poria cocos* epidermis extract obtained from A-3 was determined by liquid chromatography coupled to diode array UV detection and mass spectrometer (LC/UV/MS) at 243 nm and 210 nm wavelength respectively, and the content of each component contained in the extract were quantified by high performance liquid chromatography (HPLC). The results are shown in Table 1.

TABLE 1

| Component | wt % |
| --- | --- |
| Pachymic acid (PA) | — |
| Dehydropachymic acid (DPA) | — |
| Tumulosic acid (TA) | — |
| Dehydrotumulosic acid (DTA) | 0.46 |
| Polyporenic acid C (PAC) | 2.01 |
| 3-epi-dehydrotumulosic acid (EDTA) | 0.77 |
| Dehydrotrametenolic acid (DTTA) | 2.01 |
| Trametenolic acid (TTA) | 0.85 |
| Poricoic acid A (PAA) | 32.72 |
| Dehydroeburicoic acid (DEA) | 1.20 |
| Poricoic acid B (PAB) | 10.44 |
| Eburicoic acid (EA) | 0.83 |

A-5. The *Poria cocos* epidermis and meat obtained from A-1 were combined, and the above extraction of A-2 and A-3 were repeated to obtain a *Poria cocos* extract. Thereafter, the component of the extract thus obtained was determined by the analysis method of A-4. The results show that the *Poria cocos* extract contains dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A, poricoic acid B, etc.

B. Preparation of the Active Ingredients in *Poria cocos* Extract

B-1. The *Poria cocos* extract obtained from A-5 was dispersed evenly in methanol (*Poria cocos* extract:methanol=1:500 in volume) to provide mixture. Then, the mixture was filtrated to remove the insoluble. The remaining filtrate was purified by preparative high performance liquid chromatography (with a mobile phase of a mixture of methanol and water) at 243 nm and 210 nm wavelength respectively, and the portion of dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A and poricoic acid B was collected. The collected portion was vacuum-concentrated to remove methanol and obtain dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A and poricoic acid B respectively.

B-2. The dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A and poricoic acid B obtained from B-1 were detected by liquid chromatography coupled to diode array UV detection and mass spectrometer (LC/UV/MS) at 243 nm and 210 nm wavelength respectively, and the results show that the purities of all the components were higher than 98%.

C. Cell Cultivation

The normal primary human skin fibroblastic cells (purchased from ATCC) were cultivated in a Fibroblast Growth Medium. The cells thus provided were used in the following experiments.

Example 1

Effects of *Poria cocos* Extract on the Collagen and Hyaluronic Acid Expression Capabilities of Cells The normal primary human skin fibroblastic cells provided by [Preparation Example C] were divided into 4 groups and were respectively cultivated with the following medium for 48 hours:

1. Group I: a Fibroblast Growth Medium;
2. Group II: a Fibroblast Growth Medium containing 0.005 μg/ml *Poria cocos* epidermis extract obtained from [Preparation Example A-3];
3. Group III: a Fibroblast Growth Medium containing 0.05 μg/ml *Poria cocos* epidermis extract obtained from [Preparation Example A-3];
4. Group IV: a Fibroblast Growth Medium containing 0.5 μg/ml *Poria cocos* epidermis extract obtained from [Preparation Example A-3].

Thereafter, the cell medium of each group was collected and concentrated. Then, the intracellular content of collagen, the content of collagen in cell medium (i.e., extracellular content of collagen) and the content of hyaluronic acid in cell medium were measured and analyzed by Western blot and enzyme-linked immunosorbent assay (ELISA). Finally, the results of the control group (i.e., cells being cultivated with the medium of Group I) was taken as 100% and served as a basis to calculate the relative contents (shown as percentage) of collagen and hyaluronic acid of other groups. The results are shown in Table 2.

TABLE 2

| | Group II | Group III | Group IV |
| --- | --- | --- | --- |
| Intracellular collagen (%) | 152 | 182 | 200 |
| Collagen in cell medium (%) | 116 | 156 | 135 |
| Hyaluronic acid in cell medium (%) | 131 | 121 | 106 |

As shown in Table 2, as compared to the control group, cells being treated with the *Poria cocos* extract of the present invention (i.e., cells being cultivated with the medium of Group II, III or IV) had significantly enhanced intracellular contents of collagen, content of collagen in cell medium (i.e., extracellular content of collagen) and content of hyaluronic acid in the cell medium. The above results show that the *Poria cocos* extract of the present invention can effectively enhance the expression of collagen and/or hyaluronic acid in fibroblasts (i.e., enhancing the content of endogenous collagen and/or hyaluronic acid), and thus can be used for at least one of protecting skin and promoting wound healing.

Example 2

Effects of the Active Ingredients of *Poria cocos* Extract on the Collagen and Hyaluronic Acid Expressive Capabilities of Cells (2-1) The Intracellular Expression of Collagen The normal primary human skin fibroblastic cells provided by [Preparation Example C] were divided into 37 groups and were respectively cultivated with the following medium for 48 hours:
1. Group 1: a Fibroblast Growth Medium
2. Group 2-1 to 2-3: Fibroblast Growth Media containing the pachymic acid (PA) provided by [Preparation Example B] at a concentration of 0.01, 0.1 and 1 µM, respectively;
3. Group 3-1 to 3-3: Fibroblast Growth Media containing the dehydropachymic acid (DPA) provided by [Preparation Example B] at a concentration of 0.01, 0.1 and 1 µM, respectively;
4. Group 4-1 to 4-3: Fibroblast Growth Media containing the tumulosic acid (TA) provided by [Preparation Example B] at a concentration of 0.01, 0.1 and 1 µM, respectively;
5. Group 5-1 to 5-3: Fibroblast Growth Media containing the dehydrotumulosic acid (DTA) provided by [Preparation Example B] at a concentration of 0.01, 0.1 and 1 µM, respectively;
6. Group 6-1 to 6-3: Fibroblast Growth Media containing the polyporenic acid C (PAC) provided by [Preparation Example B] at a concentration of 0.01, 0.1 and 1 µM, respectively;
7. Group 7-1 to 7-3: Fibroblast Growth Media containing the 3-epi-dehydrotumulosic acid (EDTA) provided by [Preparation Example B] at a concentration of 0.01, 0.1 and 1 µM, respectively;
8. Group 8-1 to 8-3: Fibroblast Growth Media containing the dehydrotrametenolic acid (DTTA) provided by [Preparation Example B] at a concentration of 0.01, 0.1 and 1 µM, respectively;
9. Group 9-1 to 9-3: Fibroblast Growth Media containing the trametenolic acid (TTA) provided by [Preparation Example B] at a concentration of 0.01, 0.1 and 1 µM, respectively;
10. Group 10-1 to 10-3: Fibroblast Growth Media containing the poricoic acid A (PAA) provided by [Preparation Example B] at a concentration of 0.01, 0.1 and 1 µM, respectively;
11. Group 11-1 to 11-3: Fibroblast Growth Media containing the dehydroeburicoic acid (DEA) provided by [Preparation Example B] at a concentration of 0.01, 0.1 and 1 µM, respectively;
12. Group 12-1 to 12-3: Fibroblast Growth Media containing the poricoic acid B (PAB) provided by [Preparation Example B] at a concentration of 0.01, 0.1 and 1 µM, respectively;
13. Group 13-1 to 13-3: Fibroblast Growth Media containing the eburicoic acid (EA) provided by [Preparation Example B] at a concentration of 0.01, 0.1 and 1 µM, respectively.

Thereafter, the cell medium of each group was collected and concentrated. Then, the intracellular content of collagen was measured and analyzed by Western blot and enzyme-linked immunosorbent assay (ELISA). Finally, the results of the control group (i.e., cells being cultivated with the medium of Group 1) was taken as 100% and served as a basis to calculate the relative content (shown as percentage) of collagen of other groups. The results are shown in Table 3.

TABLE 3

| Active ingredient | Concentration | | |
|---|---|---|---|
| | 0.01 µM | 0.1 µM | 1 µM |
| Pachymic acid (PA) | 172% | 235% | 211% |
| Dehydropachymic acid (DPA) | 154% | 188% | 122% |
| Tumulosic acid (TA) | 148% | 127% | 147% |
| Dehydrotumulosic acid (DTA) | 159% | 156% | 127% |
| Polyporenic acid C (PAC) | 162% | 182% | 200% |
| 3-epi-dehydrotumulosic acid (EDTA) | 87% | 100% | 80% |
| Dehydrotrametenolic acid (DTTA) | 190% | 174% | 118% |
| Trametenolic acid (TTA) | 95% | 79% | 79% |
| Poricoic acid A (PAA) | 78% | 104% | 115% |
| Dehydroeburicoic acid (DEA) | 94% | 80% | 77% |
| Poricoic acid B (PAB) | 105% | 108% | 99% |
| Eburicoic acid (EA) | 102% | 97% | 95% |

As shown in Table 3, as compared to the control group, the cells being treated with the pachymic acid, dehydropachymic acid, tumulosic acid, dehydrotumulosic acid, polyporenic acid C, dehydrotrametenolic acid or poricoic acid A had significantly enhanced intracellular contents of collagen. The above results show that the pachymic acid, dehydropachymic acid, tumulosic acid, dehydrotumulosic acid, polyporenic acid C, dehydrotrametenolic acid and poricoic acid A, can effectively enhance the expression of collagen in fibroblasts (i.e., enhancing the content of endogenous collagen and/or hyaluronic acid), and thus, can be used for at least one of protecting skin and promoting wound healing.

(2-2) The Extracellular Expression of Collagen

To understand the effects of the active ingredients of the present invention on the extracellular expression of collagen, the concentrated cell medium of each group provided by Example (2-1) was measured and analyzed by Western blot and enzyme-linked immunosorbent assay (ELISA). The content of collagen in the medium of each group (i.e., extracellular content of collagen) was provided. Finally, the results of the control group (i.e., cells being cultivated with the medium of Group 1) was taken as 100% and served as a basis to calculate the relative content (shown as percentage) of collagen of other groups. The results are shown in Table 4.

TABLE 4

| Active ingredient | Concentration | | |
|---|---|---|---|
| | 0.01 µM | 0.1 µM | 1 µM |
| Pachymic acid (PA) | 117% | 116% | 106% |
| Dehydropachymic acid (DPA) | 124% | 122% | 116% |
| Tumulosic acid (TA) | 140% | 136% | 141% |
| Dehydrotumulosic acid (DTA) | 122% | 105% | 139% |
| Polyporenic acid C (PAC) | 134% | 162% | 153% |
| 3-epi-dehydrotumulosic acid (EDTA) | 98% | 104% | 111% |
| Dehydrotrametenolic acid (DTTA) | 117% | 158% | 131% |
| Trametenolic acid (TTA) | 141% | 149% | 142% |
| Poricoic acid A (PAA) | 111% | 111% | 91% |
| Dehydroeburicoic acid (DEA) | 143% | 148% | 185% |
| Poricoic acid B (PAB) | 122% | 136% | 153% |
| Eburicoic acid (EA) | 108% | 106% | 88% |

As shown in Table 4, as compared to the control group, the cells that were treated with the dehydropachymic acid, pachymic acid, dehydrotumulosic acid, tumulosic acid, polyporenic acid C, 3-epi-dehydrotumulosic acid, dehydrotrametenolic acid, trametenolic acid, dehydroeburicoic acid, eburicoic acid, poricoic acid A and poricoic acid B had significantly enhanced extracellular contents of collagen. The above results show that the active ingredients of the present invention can effectively enhance the expression of collagen in fibroblasts, and thus, can be used for at least one of protecting skin and promoting wound healing.

(2-3) The Extracellular Expression of Hyaluronic Acid

To understand the effects of the active ingredients of the present invention on the extracellular expression of hyaluronic acid, the concentrated cell medium of each group provided by Example (2-1) was measured and analyzed by Western blot and enzyme-linked immunosorbent assay (ELISA). The content of hyaluronic acid in the medium of each group (i.e., extracellular content of hyaluronic acid) was provided. Finally, the results of the control group (i.e., cells being cultivated with the medium of Group 1) was taken as 100% and served as a basis to calculate the relative content (shown as percentage) of hyaluronic acid of other groups. The results are shown in Table 5.

TABLE 5

| Active ingredient | Concentration | | |
|---|---|---|---|
| | 0.01 μM | 0.1 μM | 1 μM |
| Pachymic acid (PA) | 98% | 132% | 140% |
| Dehydropachymic acid (DPA) | 111% | 131% | 152% |
| Tumulosic acid (TA) | 100% | 123% | 124% |
| Dehydrotumulosic acid (DTA) | 112% | 134% | 168% |
| Polyporenic acid C (PAC) | 93% | 113% | 98% |
| 3-epi-dehydrotumulosic acid (EDTA) | 105% | 122% | 140% |
| Dehydrotrametenolic acid (DTTA) | 99% | 87% | 108% |
| Trametenolic acid (TTA) | 83% | 108% | 125% |
| Poricoic acid A (PAA) | 108% | 106% | 99% |
| Dehydroeburicoic acid (DEA) | 115% | 118% | 128% |
| Poricoic acid B (PAB) | 109% | 104% | 84% |
| Eburicoic acid (EA) | 94% | 107% | 120% |

As shown in Table 5, as compared to the control group, the cells that were treated with dehydropachymic acid, pachymic acid, dehydrotumulosic acid, tumulosic acid, polyporenic acid C, 3-epi-dehydrotumulosic acid, trametenolic acid, dehydroeburicoic acid, eburicoic acid, poricoic acid A or poricoic acid B had significantly enhanced intracellular contents of hyaluronic acid. The contents of hyaluronic acid in cells that were treated with pachymic acid, dehydropachymic acid, tumulosic acid, dehydrotumulosic acid or 3-epi-dehydrotumulosic acid were enhanced more significantly. The above results show that the active ingredients of the present invention can effectively enhance the expression of hyaluronic acid in fibroblasts, and thus, can be used for protecting skin.

As shown in the above examples, the *Poria cocos* extract and/or its active ingredients of the present invention indeed can enhance the expressions of collagen and hyaluronic acid in cells (i.e., having the abilities to enhance the content of endogenous collagen and/or hyaluronic acid), and thus, can be used for at least one of protecting skin (including nourishing skin, tightening skin, repairing skin, retaining moisture, smoothing wrinkles, delaying skin-aging, and preventing skin-aging) and promoting wound healing.

What is claimed is:

1. A method for enhancing the expression of collagen and/or hyaluronic acid, consisting of administering to a subject in of need an effective amount of a composition consisting of (i) an active ingredient; and (ii) a toner, a buffer, a preservative, and/or a pharmaceutically acceptable carrier, wherein the active ingredient is tumulosic acid, and wherein the composition is for external use, oral administration, subcutaneous administration and/or intravenous administration.

2. The method as claimed in claim 1, wherein the active ingredient is administered to the subject at an amount sufficient to enhance the expression of collagen and hyaluronic acid.

3. The method as claimed in claim 1, wherein the active ingredient is administered to the subject at an amount sufficient to enhance the expression of collagen.

4. The method as claimed in claim 1, wherein the active ingredient is administered to the subject at an amount sufficient to enhance the expression of hyaluronic acid.

* * * * *